United States Patent
Sanpei et al.

(10) Patent No.: US 6,639,109 B1
(45) Date of Patent: Oct. 28, 2003

(54) PROCESS FOR PRODUCTION OF THIOALKYLAMINE DERIVATIVES

(75) Inventors: Osamu Sanpei, Kawachinagano (JP); Kenji Tsubata, Kawachinagano (JP)

(73) Assignee: Nihon Nohyaku Co., Ltd., Tokyo (JP)

( * ) Notice: Subject to any disclaimer, the term of this patent is extended or adjusted under 35 U.S.C. 154(b) by 0 days.

(21) Appl. No.: 10/089,114

(22) PCT Filed: Sep. 27, 2000

(86) PCT No.: PCT/JP00/06673

§ 371 (c)(1), (2), (4) Date: May 29, 2002

(87) PCT Pub. No.: WO01/23350

PCT Pub. Date: Apr. 5, 2001

(30) Foreign Application Priority Data

Sep. 28, 1999 (JP) ............................ 11-274362

(51) Int. Cl.$^7$ ............................ C07C 323/24
(52) U.S. Cl. ........................ 564/501; 564/500
(58) Field of Search ................. 564/305, 314, 564/440, 463, 500, 501

(56) References Cited

U.S. PATENT DOCUMENTS

| | | | | |
|---|---|---|---|---|
| 2,769,839 A | * | 11/1956 | Fincke ................. | 564/340 |
| 3,471,564 A | * | 10/1969 | Hickner | |
| 3,472,895 A | * | 10/1969 | Gray et al. .............. | 564/453 |
| 3,905,957 A | * | 9/1975 | Sirrenberg et al. ........ | 540/589 |
| 4,126,633 A | * | 11/1978 | Toukan et al. ............ | 562/556 |
| 4,259,334 A | | 3/1981 | Navarron | |
| 5,405,947 A | * | 4/1995 | Hoppe et al. ............. | 534/618 |

FOREIGN PATENT DOCUMENTS

| | | |
|---|---|---|
| EP | 53015 | 6/1982 |
| EP | 66425 | 12/1982 |
| EP | 66993 | 12/1982 |
| EP | 468434 | 1/1992 |
| GB | 1469772 | 4/1977 |
| GB | 1527510 | 10/1978 |
| GB | 1604674 | 12/1981 |
| WO | WO 89/10919 | 11/1989 |
| WO | WO 95/00493 | 1/1995 |
| WO | WO 99/50238 | 10/1999 |

OTHER PUBLICATIONS

CA:96:67897 abs of Zhurnal Priklodnoi Khimii by Krivonogov et al 54(11) pp 2505–2510 1981.*
CA:132:93843 abs of Zhurnal Prikladnoi Khimii 72(2) pp 259–267 1999.*
CA:124:174972 abs of Tetrahedron Letters by Richardson 36(51) pp 9241–9244 1995.*

* cited by examiner

Primary Examiner—Jean F. Vollano
(74) Attorney, Agent, or Firm—Paul E. White, Jr.; Manelli Denison & Selter PLLC

(57) ABSTRACT

The present invention relates to a thioalkylamine derivative represented by general formula (I); and a process for production thereof:

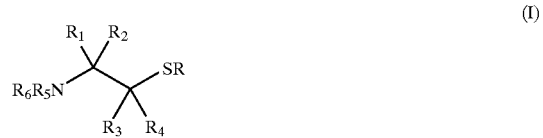

wherein each of $R_1$ and $R_2$ is H, $(C_1-C_4)$alkyl, $(C_3-C_8)$cycloalkyl, $(C_3-C_8)$cycloalkyl$(C_1-C_4)$alkyl, (substituted) phenyl, (substituted) phenyl$(C_1-C_4)$alkyl, or the like; each of $R_3$ and $R_4$ is H or a $(C_1-C_4)$alkyl group; each of $R_5$ and $R_6$ is H, $(C_1-C_4)$alkyl, a (substituted) phenyl group or a (substituted) phenyl$(C_1-C_4)$alkyl group; alternatively each of $R_1$ and $R_2$, $R_1$ and $R_3$ or $R_5$, $R_3$ and $R_4$, $R_3$ and $R_5$ or $R_5$ and $R_6$ may together form lower alkylene; and R is $(C_1-C_{12})$alkyl, $(C_3-C_8)$cycloalkyl, $(C_3-C_8)$cycloalkyl$(C_1-C_4)$alkyl, (substituted) phenyl, (substituted) phenyl$(C_1-C_4)$alkyl, a naphthyl group, a (substituted) aromatic heterocyclic, or the like.

2 Claims, No Drawings

PROCESS FOR PRODUCTION OF THIOALKYLAMINE DERIVATIVES

This application is a 371 of PCT/JP00/06673 filed Sep. 27, 2000, now Ser. No. WO 01/23350.

TECHNICAL FIELD

The present invention relates to thioalkylamine derivatives represented by general formula (I) which are useful as intermediates of medicines, agrochemicals, chemical products, etc., and a process for production of the derivatives.

BACKGROUND ART

Thioalkylamine derivatives are useful as intermediates for synthesis of agrochemicals, medicines, chemical products, etc. or starting materials for them. When used in agrochemicals, the derivatives are useful compounds as, for example, starting compounds for the agricultural and horticultural insecticide disclosed in Japanese Patent Application No. 11-338715 filed by the same applicant as the present applicant.

Thioalkylamines can be classified into thiols and sulfides according to chemical structure. As a process for producing any of the thiols and the sulfides, the following processes have been reported.

(1) A process in which a thiol is produced by hydrolyzing a thiazoline or thiazolidinone derivative (for example, J. Med. Chem., 1965, 8, 762; JP-A-59-231064; Bull. Soc. Chim. Fr. 1967, 3637; and Z. Naturforsch., B: Chem. Sci. 1987, 42, 348). (2) A process in which a sulfide is produced by reacting an oxazoline or oxazolidinone derivative with a thiol (for example, J. Org. Chem., 1992, 57,6257; and J. Med. Chem., 1984, 27, 1354). (3) A process in which a sulfide or a thiol is produced by reacting an aziridine with a sulfur compound such as a mercaptan (for example, Tetrahedron, 1992, 48, 2359; J. Am. Chem. Soc., 1986, 108,.3811; Inorg. Chem., 1984, 23, 3404; and Tetrahedron Lett., 1983, 24, 2131). (4) A process in which a sulfide is produced by hydrolyzing an amide obtained by reacting an amino alcohol with a mercaptan in a carboxylic acid (for example, Neth. Appl. 6, 404, 644). (5) A process in which a thiol is produced by reacting an amino alcohol sulfate ester with ammonium hydrogensulfide (for example, Journal of Chemical Society of Japan, 1979, 149). (6) A process in which a thioalkyl alcohol is converted to a thioalkylamine by Ritter reaction and hydrolysis (for example, Ger. Offen. 2,045,905).

A desired compound in the present invention is a sulfide as a thioalkylamine. Therefore, of the above prior arts, the production processes (2), (3), (4) and (6) are closely concerned with the desired compound. However, the process (2) involves, for example, the following problem: it requires a hydrolysis step because the product is obtained as an amide, and the reaction does not take place if a substituent such as an alkyl group is present in the oxazolidine ring of the starting compound. This process is also disadvantageous in that only an aromatic sulfide can be produced owing to the acidity of a mercapto group. The process (3) is not suitable for industrial adoption from the viewpoint of safety and facilities because the aziridine whose toxicity tends to affect the health of production workers is used after its production and isolation. The process (4) is disadvantageous, for example, in that the product is limited to a thiol because the reaction is carried out with heating under pressure for a long period of time. Moreover, this process is disadvantageous, for example, in that like the process (2), it requires hydrolysis because the product is obtained as an amide. The process (6) is disadvantageous, for example, in that an excess of prussic acid is used which is very toxic and requires great care in handling and after-treatment, or that the hydrolysis is not easy when an easily handleable nitrile is used.

Although the processes (1) and (5) are production processes of a thiol and are not directly concerned with a process for producing a sulfide intended according to the present invention, they involve the following problems. That is, the process (1) is industrially disadvantageous from the viewpoint of the number of steps and yield because the thiazoline or thiazolidinone derivative should be produced. The process (5) is industrially disadvantageous in that it entails high cost in view of facilities and production efficiency because the reaction is carried out in a sealed tube for a long period of time.

The present invention avoids, for example, the following various problems in prior arts: a reaction is carried out at a high temperature and a high pressure for a long period of time; an additional step such as hydrolysis is needed; there are various restrictions on introducible substituents; and the toxicity of a starting material used and the like is so high that safety and facilities required for handling and after-treatment of the staring material and the like cost a great deal. Thus, the present invention provides a production process which is simple and short, can be generally adopted, can be safely practiced, and is economically advantageous.

DISCLOSURE OF THE INVENTION

In order to solve the above problems and develop a novel process for producing a thioalkylamine, the present inventors earnestly investigated and consequently found that the above object can be achieved by producing a sulfate ester represented by general formula (III) by the reaction of an amino alcohol represented by general formula (II) with sulfuric acid, and reacting the sulfate ester with a mercaptan under basic conditions, whereby the present invention has been accomplished.

The present invention relates to a thioalkylamine derivative represented by general formula (I):

wherein each of $R_1$ and $R_2$, which may be the same or different, is a hydrogen atom; a $(C_1-C_4)$alkyl group; a $(C_3-C_8)$cycloalkyl group; a $(C_3-C_8)$cycloalkyl$(C_1-C_4)$alkyl group; a hydroxy-$(C_1-C_4)$alkyl group; a phenyl group; a substituted phenyl group having 1 to 5 substituents which may be the same or different and each of the substituents is selected from a halogen atom, a cyano group, a nitro group, a $(C_1-C_4)$alkyl group, a halo$(C_1-C_4)$alkyl group, a $(C_3-C_8)$cycloalkyl group, a $(C_1-C_4)$alkoxy group, a halo$(C_1-C_4)$alkoxy group, a $(C_1-C_4)$alkylthio group, a halo$(C_1-C_4)$alkylthio group, a $(C_1-C_4)$alkylsulfinyl group, a halo$(C_1-C_4)$alkylsulfinyl group, a $(C_1-C_4)$alkylsulfonyl group, a halo$(C_1-C_4)$alkylsulfonyl group, a carboxyl group, a $(C_1-C_4)$alkoxycarbonyl group, a $(C_1-C_4)$alkoxy$(C_1-C_4)$alkyl group, $R_7—C(=O)—$ (wherein $R_7$ is a $(C_1-C_4)$alkyl group, a halo$(C_1-C_4)$alkyl group, a phenyl group or a phenoxy group), an amino group, and a substituted amino group having one or two substituents which may be the same or different and are selected from $(C_1-C_4)$alkyl groups; a substituted phenyl group having as the substituent a $(C_3-C_4)$ alkylene group or a $(C_1-C_2)$alkylenedioxy group, which forms a ring together with a pair of adjacent carbon atoms in the benzene ring; a phenyl$(C_1-C_4)$alkyl group; or a substituted phenyl$(C_1-C_4)$alkyl group having on the ring 1 to 5 substituents which may be the same or different and each of the substituents is selected from a halogen atom, a cyano group, a nitro group, a $(C_1-C_4)$alkyl group, a halo$(C_1-C_4)$alkyl group, a $(C_3-C_8)$cycloalkyl group, a $(C_1-C_4)$ alkoxy group, a halo$(C_1-C_4)$alkoxy group, a $(C_1-C_4)$ alkylthio group, a halo$(C_1-C_4)$alkylthio group, a $(C_1-C_4)$ alkylsulfinyl group, a halo$(C_1-C_4)$alkylsulfinyl group, a $(C_1-C_4)$alkylsulfonyl group and a halo$(C_1-C_4)$alkylsulfonyl group; $R_1$ and $R_2$ may form a $(C_2-C_5)$alkylene group by binding to each other; $R_1$ and $R_3$ or $R_5$ may form a $(C_3-C_5)$alkylene group by binding to each other, each of $R_3$ and $R_4$, which may be the same or different, is a hydrogen atom or a $(C_1-C_4)$alkyl group; $R_3$ and $R_4$ may form a $(C_4-C_6)$alkylene group by binding to each other; $R_3$ and $R_5$ may form a $(C_2-C_4)$alkylene group by binding to each other, each of $R_5$ and $R_6$, which may be the same or different, is a hydrogen atom; a $(C_1-C_4)$alkyl group; a phenyl group; a substituted phenyl group having 1 to 5 substituents which may be the same or different and each of the substituents is selected from a halogen atom, a cyano group, a nitro group, a $(C_1-C_4)$alkyl group, a halo$(C_1-C_4)$alkyl group, a $(C_3-C_8)$cycloalkyl group, a $(C_1-C_4)$alkoxy group, a halo$(C_1-C_4)$alkoxy group, a $(C_1-C_4)$alkylthio group, a halo$(C_1-C_4)$alkylthio group, a $(C_1-C_4)$alkylsulfinyl group, a halo$(C_1-C_4)$ alkylsulfinyl group, a $(C_1-C_4)$alkylsulfonyl group and a halo$(C_1-C_4)$alkylsulfonyl group; a phenyl$(C_1-C_4)$ alkyl group; or a substituted phenyl$(C_1-C_4)$alkyl group having on the ring 1 to 5 substituents which may be the same or different and each of the substituents is selected from a halogen atom, a cyano group, a nitro group, a $(C_1-C_4)$ alkyl group, a halo$(C_1-C_4)$alkyl group, a $(C_3-C_8)$cycloalkyl group, a $(C_1-C_4)$alkoxy group, a halo$(C_1-C_4)$alkoxy group, a $(C_1-C_4)$alkylthio group, a halo$(C_1-C_4)$alkylthio group, a $(C_1-C_4)$alkylsulfinyl group, a halo$(C_1-C_4)$alkylsulfinyl group, a $(C_1-C_4)$ alkylsulfonyl group and a halo$(C_1-C_4)$alkylsulfonyl group; $R_5$ and $R_6$ may form a $(C_4-C_6)$alkylene group by binding to each other, and R is a $(C_1-C_{12})$alkyl group; a $(C_3-C_8)$cycloalkyl group; a $(C_3-C_8)$cycloalkyl$(C_1-C_4)$alkyl group; a phenyl group; a substituted phenyl group having 1 to 5 substituents which may be the same or different and each of the substituents is selected from a halogen atom, a $(C_1-C_6)$ alkyl group, a halo$(C_1-C_3)$alkyl group, a $(C_3-C_8)$ cycloalkyl group, a $(C_1-C_4)$alkoxy group and a halo $(C_1-C_4)$alkoxy group; a phenyl$(C_1-C_4)$alkyl group; a substituted phenyl$(C_1-C_4)$alkyl group having on the ring 1 to 5 substituents which may be the same or different and each of the substituents is selected from a halogen atom and a $(C_1-C_4)$alkyl group; a naphthyl group; an aromatic heterocyclic group; or a substituted aromatic heterocyclic group having one or more substituents which may be the same or different and each of the substituents is selected from a halogen atom, a $(C_1-C_4)$alkyl group, a $(C_1-C_4)$alkoxy group, a phenyl group, and a substituted phenyl group having 1 to 5 substituents which may be the same or different and each of the substituents is selected from a halogen atom and a $(C_1-C_4)$alkyl group, provided that:

(1) when $R_1$, $R_2$, $R_3$, $R_4$, $R_5$ and $R_6$ are hydrogen atoms at the same time, then R is not a $(C_1-C_6)$alkyl group, phenyl group and aromatic heterocyclic group of 2-furyl group, 2-thienyl group, 2-thiazolyl group, 2-imidazolyl group, 2-pyridyl group and 2-pyrimidinyl group.

(2) when $R_1$, $R_2$, $R_3$, $R_4$ and $R_6$ are hydrogen atoms at the same time and $R_5$ is a $(C_1-C_4)$alkyl group or a phenyl group, then R is not a $(C_1-C_4)$alkyl group, phenyl group and aromatic heterocyclic group of pyridyl group and pyrimidinyl group.

(3) when $R_1$, $R_2$, $R_3$ and $R_4$ are hydrogen atoms at the same time and each of $R_5$ and $R_6$ is a $(C_1-C_4)$alkyl group or a phenyl group, then R is not a $(C_1-C_5)$alkyl group, phenyl group and aromatic heterocyclic group of triazolyl group, tetrazolyl group, 1,2,3-thiadiazolyl group, pyridyl group, 2-pyrimidinyl group and pyrazinyl group, (4) when $R_2$, $R_3$, $R_4$, $R_5$ and $R_6$ are hydrogen atoms at the same time and R is a phenyl group, then $R_1$ is not a $(C_1-C_4)$alkyl group and phenyl group, (5) when $R_2$, $R_3$, $R_4$, $R_5$ and $R_6$ are hydrogen atoms at the same time and $R_1$ is a methyl group, then R is not a methyl group and aromatic heterocyclic group of 2-benzothiazolyl group, (6) when $R_2$, $R_3$, $R_4$ and $R_6$ are hydrogen atoms at the same time, $R_1$ is a methyl group and R is a methyl group, then $R_5$ is not a $(C_1-C_3)$alkyl group and phenyl group, (7) when $R_2$, $R_3$, $R_4$, $R_5$ and $R_6$ are hydrogen atoms at the same time and $R_1$ is an ethyl group, then R is not an aromatic heterocyclic group of 2-indolyl group, (8) when $R_2$, $R_3$, $R_4$ and $R_5$ are hydrogen atoms at the same time, $R_6$ is a phenyl group and $R_1$ is a methyl group, then R is not a methyl group and t-butyl group, (9) when $R_2$, $R_3$, $R_4$ and $R_5$ are hydrogen atoms at the same time, $R_6$ is a phenyl group and $R_1$ is a propyl group, then R is not a methyl group and phenyl group,

(10) when $R_2$, $R_3$ and $R_4$ are hydrogen atoms at the same time, each of $R_5$ and $R_6$ is a methyl group, a propyl group or a phenyl group and $R_1$ is a methyl group, then R is not a methyl group, t-butyl group and phenyl group,

(11) when $R_2$, $R_3$ and $R_4$ are hydrogen atoms at the same time, $R_5$ and $R_6$ are methyl groups at the same time and $R_1$ is a propyl group, then R is not an ethyl group and phenyl group,

(12) when $R_2$, $R_3$, $R_4$ and $R_5$ are hydrogen atoms at the same time, $R_1$ is a phenyl group and R is a methyl group or a phenyl group, then $R_6$ is not a methyl group, n-propyl group and phenyl group,

(13) when $R_2$, $R_3$, $R_4$ and $R_5$ are hydrogen atoms at the same time, $R_1$ is a phenyl group and R is a butyl group, then $R_6$ is not a hydrogen atom and methyl group,

(14) when $R_2$, $R_3$ and $R_4$ are hydrogen atoms at the same time, $R_5$ and $R_6$ are methyl groups at the same time and $R_1$ is a phenyl group, then R is not a methyl group and phenyl group,

(15) when $R_1$, $R_2$, $R_4$, $R_5$ and $R_6$ are hydrogen atoms at the same time and $R_3$ is a methyl group, then R is not a methyl group and phenyl group,

(16) when $R_1$, $R_2$ and $R_4$ are hydrogen atoms at the same time, $R_3$ is a $(C_1-C_4)$alkyl group and each of $R_5$ and $R_6$ is a methyl group, an ethyl group or a phenyl group, then R is not a $(C_1-C_3)$alkyl group and phenyl group,

(17) when $R_3$, $R_4$, $R_5$ and $R_6$ are hydrogen atoms at the same time and $R_1$ and $R_2$ are methyl groups at the same time, then R is not a methyl group, ethyl group and phenyl group,

(18) when $R_3$, $R_4$, $R_5$ and $R_6$ are hydrogen atoms at the same time and $R_1$ and $R_2$ are n-propyl groups at the same time, then R is not a methyl group,

(19) when $R_3$, $R_4$, $R_5$ and $R_6$ are hydrogen atoms at the same time, $R_1$ is an ethyl group and $R_2$ is an n-butyl group, then R is not an aromatic heterocyclic group of 2-thienyl group,

(20) when $R_3$, $R_4$ and $R_6$ are hydrogen atoms at the same time, $R_1$ and $R_2$ are methyl groups at the same time and $R_5$ is a phenyl group, then R is not a phenyl group,

(21) when $R_3$ and $R_4$ are hydrogen atoms at the same time and $R_1$, $R_2$, $R_5$ and $R_6$ are methyl groups at the same time, then R is not a methyl group,

(22) when $R_1$, $R_2$, $R_5$ and $R_6$ are hydrogen atoms at the same time and $R_3$ and $R_4$ are methyl groups at the same time, then R is not a methyl group,

(23) when $R_1$, $R_2$ and $R_6$ are hydrogen atoms at the same time, $R_3$ and $R_4$ are methyl groups at the same time and $R_5$ is a t-butyl group, then R is not a phenyl group,

(24) when $R_1$ and $R_2$ are hydrogen atoms at the same time and $R_3$, $R_4$, $R_5$ and $R_6$ are methyl groups at the same time, then R is not a methyl group,

(25) when $R_2$, $R_4$, $R_5$ and $R_6$ are hydrogen atoms at the same time, $R_1$ is a methyl group, an ethyl group or a phenyl group and $R_3$ is a methyl group, then R is not a methyl group and phenyl group,

(26) when $R_2$, $R_4$, $R_5$ and $R_6$ are hydrogen atoms at the same time, $R_1$ is a $(C_1-C_4)$alkyl group and $R_3$ is an n-butyl group, then R is not a methyl group,

(27) when $R_2$, $R_4$ and $R_6$ are hydrogen atoms at the same time, $R_1$ is an ethyl group and $R_3$ and R are methyl groups at the same time, then $R_5$ is not a methyl group and ethyl group,

(28) when $R_2$ and $R_4$ are hydrogen atoms at the same time, each of $R_1$ and $R_6$ is a methyl group or an ethyl group and $R_3$ and $R_5$ are methyl groups at the same time, then R is not a methyl group and phenyl group, and

(29) when $R_1$ is an isopropyl group, $R_2$, $R_5$ and $R_6$ are hydrogen atoms at the same time and $R_3$ and $R_4$ are methyl groups at the same time, then R is not a methyl group. Furthermore, the present invention relates to a novel process for producing a thioalkylamine derivative represented by general formula (I):

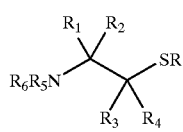

(I)

(wherein $R_1$, $R_2$, $R_3$, $R_4$, $R_5$, $R_6$ and R are as defined below) and including well-known thioalkylamine derivatives, which is characterized by reacting sulfuric acid with an amino alcohol represented by general formula (II):

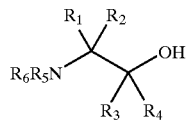

(II)

(wherein each of $R_1$ and $R_2$, which may be the same or different, is a hydrogen atom; a $(C_1-C_4)$alkyl group; a $(C_3-C_8)$cycloalkyl group; a $(C_3-C_8)$cycloalkyl$(C_1-C_4)$alkyl group; a hydroxy$(C_1-C_4)$alkyl group; a phenyl group; a substituted phenyl group having 1 to 5 substituents which may be the same or different and each of the substituents is selected from a halogen atom, a cyano group, a nitro group, a $(C_1-C_4)$alkyl group, a halo$(C_1-C_4)$alkyl group, a $(C_3-C_8)$cycloalkyl group, a $(C_1-C_4)$alkoxy group, a halo$(C_1-C_4)$alkoxy group, a $(C_1-C_4)$alkylthio group, a halo$(C_1-C_4)$alkylthio group, a $(C_1-C_4)$alkylsulfinyl group, a halo$(C_1-C_4)$alkylsulfinyl group, a $(C_1-C_4)$alkylsulfonyl group, a halo$(C_1-C_4)$alkylsulfonyl group, a carboxyl group, a $(C_1-C_4)$alkoxycarbonyl group, a $(C_1-C_4)$alkoxy$(C_1-C_4)$alkyl group, $R_7-C(=O)-$ (wherein $R_7$ is a $(C_1-C_4)$alkyl group, a halo$(C_1-C_4)$alkyl group, a phenyl group or a phenoxy group), an amino group, and a substituted amino group having one or two substituents which may be the same or different and are selected from $(C_1-C_4)$alkyl groups; a substituted phenyl group having as the substituent a $(C_3-C_4)$alkylene group or a $(C_1-C_2)$alkylenedioxy group, which forms a ring together with a pair of adjacent carbon atoms in the benzene ring; a phenyl$(C_1-C_4)$alkyl group; or a substituted phenyl$(C_1-C_4)$alkyl group having on the ring 1 to 5 substituents which may be the same or different and each of the substituents is selected from a halogen atom, a cyano group, a nitro group, a $(C_1-C_4)$alkyl group, a halo $(C_1-C_4)$alkyl group, a $(C_3-C_8)$cycloalkyl group, a $(C_1-C_4)$alkoxy group, a halo$(C_1-C_4)$alkoxy group, a $(C_1-C_4)$alkylthio group, a halo$(C_1-C_4)$alkylthio group, a $(C_1-C_4)$alkylsulfinyl group, a halo$(C_1-C_4)$alkylsulfinyl group, a $(C_1-C_4)$alkylsulfonyl group and a halo$(C_1-C_4)$alkylsulfonyl group; $R_1$ and $R_2$ may form a $(C_2-C_4)$alkylene group by binding to each other; $R_1$ and $R_3$ or $R_5$ may form a $(C_3-C_5)$alkylene group by binding to each other, each of $R_3$ and $R_4$, which may be the same or different, is a hydrogen atom or a $(C_1-C_4)$alkyl group; $R_3$ and $R_4$ may form a $(C_4-C_6)$alkylene group by binding to each other; $R_3$ and $R_5$ may form a $(C_2-C_4)$alkylene group by binding to each other, each of $R_5$ and $R_6$, which may be the same or different, is a hydrogen atom; a $(C_1-C_4)$alkyl group; a phenyl group; a substituted phenyl group having 1 to 5 substituents which may be the same or different and each of the substituents is selected from a halogen atom, a cyano group, a nitro group, a $(C_1-C_4)$alkyl group, a halo$(C_1-C_4)$alkyl group, a $(C_3-C_8)$cycloalkyl group, a $(C_1-C_4)$alkoxy group, a halo$(C_1-C_4)$alkoxy group, a $(C_1-C_4)$alkylthio group, a halo$(C_1-C_4)$alkylthio group, a $(C_1-C_4)$alkylsulfinyl group, a halo$(C_1-C_4)$ alkylsulfinyl group, a $(C_1-C_4)$alkylsulfonyl group and a halo$(C_1-C_4)$alkylsulfonyl group; a phenyl$(C_1-C_4)$ alkyl group; or a substituted phenyl$(C_1-C_4)$alkyl group having on the ring 1 to 5 substituents which may be the same or different and each of the substituents is selected from a halogen atom, a cyano group, a nitro group, a $(C_1-C_4)$alkyl group, a halo$(C_1-C_4)$alkyl group, a $(C_3-C_8)$cycloalkyl group, a $(C_1-C_4)$alkoxy group, a halo$(C_1-C_4)$alkoxy group, a $(C_1-C_4)$alkylthio group, a halo($C_1$–$C_4$)alkylthio group, a ($C_1$–$C_4$)alkylsulfinyl group, a halo($C_1$–$C_4$)alkylsulfinyl group, a ($C_1$–$C_4$)alkylsulfonyl group and a halo($C_1$–$C_4$)alkylsulfonyl group; and $R_5$ and $R_6$ may form a ($C_4$–$C_6$)alkylene group by binding to each other) to obtain a sulfate ester represented by general formula (III):

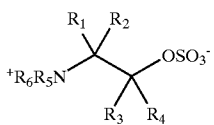

(III)

(wherein $R_1$, $R_2$, $R_3$, $R_4$, $R_5$ and $R_6$ are as defined above), and reacting the sulfate ester, after or without isolation, with a mercaptan represented by general formula (IV):

RSM     (IV)

(wherein R is a ($C_1$–$C_{12}$)alkyl group; a ($C_3$–$C_8$)cycloalkyl group; a ($C_3$–$C_8$)cycloalkyl($C_1$–$C_4$)alkyl group; a phenyl group; a substituted phenyl group having 1 to 5 substituents which may be the same or different and each of the substituents is selected from a halogen atom, a ($C_1$–$C_6$)alkyl group, a halo($C_1$–$C_3$)alkyl group, a ($C_3$–$C_7$)cycloalkyl group, a ($C_1$–$C_4$)alkoxy group and a halo($C_1$–$C_4$)alkoxy group; a phenyl($C_1$–$C_4$)alkyl group; a substituted phenyl ($C_1$–$C_4$)alkyl group having on the ring 1 to 5 substituents which may be the same or different and each of the substituents is selected from a halogen atom and a ($C_1$–$C_4$)alkyl group; a naphthyl group; an aromatic heterocyclic group; or a substituted aromatic heterocyclic group having one or more substituents which may be the same or different and each of the substituents is selected from a halogen atom, a ($C_1$–$C_4$)alkyl group, a ($C_1$–$C_4$)alkoxy group, a phenyl group and a substituted phenyl group having 1 to 5 substituents which may be the same or different and each of the substituents is selected from a halogen atom and a ($C_1$–$C_4$)alkyl group, and M is a hydrogen atom, an ammonium group or an alkali metal atom).

By the production process of the present invention, a thioalkylamine can be produced safely without directly handling a very toxic reagent, intermediate or the like. Moreover, the production process permits industrially advantageous production of said thioalkylamine without using a special reactor or the like.

MODE FOR CARRYING OUT THE INVENTION

Examples of the substituents in the present invention are given below. In the abbreviated representation of the chemical formulas in the present invention, "i-" is a prefix for "iso", "s-" is a prefix for "secondary", and "t-" is a prefix for "tertiary".

In the definition of the substituents of the thioalkylamine derivative represented by general formula (I) of the present invention, the term "halogen atom" means a chlorine atom, a bromine atom, an iodine atom or a fluorine atom. The term "($C_1$–$C_4$)alkyl" or "($C_1$–$C_6$)alkyl," means a linear or branched alkyl group of 1 to 4 carbon atoms or 1 to 6 carbon atoms, respectively, such as methyl, ethyl, n-propyl, i-propyl, n-butyl, i-butyl, s-butyl, t-butyl, n-pentyl, n-hexyl or the like. The term "halo($C_1$–$C_4$)alkyl" or "halo($C_1$–$C_6$) alkyl" means a substituted linear or branched alkyl group of 1 to 4 carbon atoms or 1 to 6 carbon atoms, respectively, having as the substituent(s) one or more halogen atoms which may be the same or different. The term "($C_3$–$C_6$)

alkylene" means a linear or branched alkylene group of 3 to 6 carbon atoms, such as propylene, trimethylene, dimethylmethylene, tetramethylene, methyltrimethylene, dimethylethylene or the like.

The aromatic heterocyclic group includes, for example, furan, thiophene, pyrrole, oxazole, oxazoline, isoxazole, thiazole, isothiazole, imidazole, pyrazole, 1,2,4-oxadiazole, 1,3,4-oxadiazole, 1,2,4-thiadiazole, 1,3,4-thiadiazole, 1,2,3-thiadiazole, 1,2,5-thiadiazole, 1,2,3-triazole, 1,2,4-triazole, tetrazole, pyridine, pyrimidine, pyridazine, pyrazine and triazine. In any of these groups, one or more nitrogen atoms in the molecule may be oxidized. In addition, benzo derivatives of these groups may also be used. The "benzo derivatives" include, for example, benzofuran, isobenzofuran, 1-benzothiophene, 2-benzothiophene, indole, isoindole, 1,2-benzothiazole, 1,3-benzothiazole, 2,1- benzothiazole, indazole, benzimidazole, quinoline, isoquinoline, quinazoline, quinoxaline, cinnoline, phthalazine, 1,2,3-benzothiadiazole, benzotriazole, benzoxazine, benzothiazine, benzopyridazine, 1-oxo-4-azanaphthalene and 1-thia-4-azanaphthalene. The substitution position(s) in the benzo derivatives is not particularly limited.

The thioalkylamine derivatives of general formula (I) of the present invention can be produced, for example, by the production process schematically shown below:

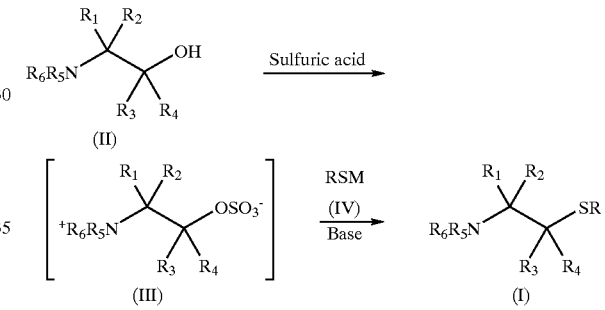

wherein $R_1$, $R_2$, $R_3$, $R_4$, $R_5$, $R_6$ and R are as defined above.

The thioalkylamine of general formula (I) can be produced by reacting an amino alcohol of general formula (II) with sulfuric acid in the presence of an inert solvent to produce a sulfate ester of general formula (III), and reacting the sulfate ester with a mercaptan of general formula (IV) in the presence of a base and an inert solvent after or without isolating the sulfate ester.

1. General Formula (II)→General Formula (III)

In the case of this reaction, the desired compound can be produced by distilling off the water from a mixed aqueous solution of the amino alcohol of general formula (II) and sulfuric acid. The desired compound can be produced by the process described, for example, in Organic Syntheses Collective Volume 3, 148 and J. Am. Chem. Soc., 1959, 81, 4689.

As the amino alcohol as staring material in the reaction, there can be used, for example, ethanolamine, 2-amino-1-propanol, 2-amino-2-methyl-1-propanol, 2-amino-1-butanol, 2-amino-1-pentanol, 2-amino-3-methyl-1-butanol, 2-amino-1-hexanol, isoleucinol, leucinol and 1-amino-1-cyclopentanemethanol.

In the reaction, an azeotropic dehydrating solvent is preferably used in order to remove continuously the water produced in the reaction system. As the azeotropic dehydrating solvent, there can be used, for example, aromatic hydrocarbons such as benzene, toluene, xylene, etc.; halogenated hydrocarbons such as chloroform, dichloroethane, trichloroethane, dichloropropane, trichloroethylene, tetrachloroethylene, fluorobenzene, chlorobenzene, dichlorobenzene, etc.; nitrated hydrocarbons such as nitromethane, nitroethane, nitropropane, etc.; nitrile type hydrocarbons such as acetonitrile, propionitrile, butyronitrile, etc.; polyether type hydrocarbons such as diglyme, propylene glycol dimethyl ether, etc.; and carbonic acid esters such as diethyl carbonate, etc.

The amount of sulfuric acid used may be 1 equivalent or more per equivalent of the amino alcohol of general formula (II). The reaction temperature may be the boiling point of the inert solvent used. When an azeotropic dehydrating solvent is used, the reaction temperature may be any temperature so long as it permits azeotropic dehydration. Although the reaction time is varied depending on the scale of reaction, the reaction may be carried out in the range of 1 to 24 hours, preferably 1 to 10 hours.

The sulfate ester of general formula (III) may be isolated and purified if necessary, or it may be used as it is in the subsequent step without isolation and purification.

2. General Formula (III)→General Formula (I)

As the mercaptan of general formula (IV) used in this reaction, there can be used, for example, methylmercaptan, ethylmercaptan, propylmercaptan, isopropylmercaptan, butylmercaptan, hexylmercaptan, cyclohexylmercaptan, octylmercaptan, decylmercaptan, dodecylmercaptan, thiophenol, thiocresol, ethylthiophenol, isopropylthiophenol, t-butylthiophenol, dimethylthiophenol, fluorothiophenol, chlorothiophenol, bromothiophenol, dichlorobenzenethiol, methoxybenzenethiol, benzylmercaptan, chlorobenzylmercaptan, t-butylbenzylmercaptan, naphthalenethiol, mercaptopyridine, 2-mercaptopyridine N-oxide, mercaptopyrimidine, dimethylmercaptopyrimidine, dimethoxymercaptopyrimidine, methylfuranthiol, furfurylmercaptan, mercaptoimidazole, 2-mercapto-1-methylimidazole, 1,2,4-triazole-3-thiol, 4-methyl-1,2,4-triazole-3-thiol, 5-methyl-1,3,4-thiadiazole-2-thiol, 4-methyl-1,2,3-thiadiazole-5-thiol and 4-t-butyl-1,2,3-thiadiazole-5-thiol. There can also be used salts of these compounds, such as alkali metal salts (e.g. sodium salts, potassium salts and lithium salts), ammonium salts, etc. As to the amount of the mercaptan used, the reaction may be carried out by choosing the amount in the range of 1 to 10 equivalents, preferably 1 to 2 equivalents, per equivalent of the sulfate ester of general formula (III).

As the base, there can be used inorganic bases such as sodium hydroxide, potassium hydroxide, sodium carbonate, potassium carbonate, etc. The amount of the base used ranges from 1 to 5 equivalents, preferably 1 to 3 equivalents, per equivalent of the sulfate ester of general formula (III).

As the inert solvent, there can be used, for example, either water or a mixed solvent of water and an organic solvent. As the organic solvent, there can be used, for example, alcohols such as methanol, ethanol, propanol, isopropanol, etc.; aromatic hydrocarbons such as benzene, toluene, xylene, etc.; halogenated hydrocarbons such as chloroform, dichloroethane, trichloroethane, dichloropropane, trichloroethylene, tetrachloroethylene, fluorobenzene, chlorobenzene, dichlorobenzene, etc.; nitrated hydrocarbons such as nitromethane, nitroethane, nitropropane, etc.; nitrile type hydrocarbons such as acetonitrile, propionitrile, butyronitrile, etc.; polyether type hydrocarbons such as diglyme, etc.; and carbonic acid esters such as diethyl carbonate, etc. The alcohols such as methanol, ethanol, etc. may be used singly or as a mixture of two or more thereof.

The reaction temperature is 50 to 150° C., preferably 65 to 100° C. Although varied depending on the scale of reaction, the reaction time ranges from several minutes to 24 hours, preferably from 1 to 10 hours.

After completion of the reaction, the desired compound is isolated from the reaction system containing the desired compound by a conventional method, and if necessary, purified, whereby the thioalkylamine derivative of general formula (I) can be produced.

When the reactions 1 and 2 are carried out in succession, the reaction 2 may be carried out by adding water, the base and the mercaptan to the reaction system without isolating the sulfate ester. As to the amount of the base used, when sulfuric acid is used in an amount of more than 1 equivalent, the amount of the base should be increased by an amount corresponding to the surplus sulfuric acid. When a mixed solvent of water or an alcohol and an organic solvent is used, the mixing ratio may be properly chosen so that the amount of water or the alcohol may be sufficient to dissolve the sulfate ester and that when a solid mercaptan is used, the amount of the organic solvent is sufficient to dissolve this mercaptan. When the mercaptan is liquid, the reaction 2 can be carried out without using an organic solvent, though it is preferable to use an organic solvent properly when a mercaptan having a low boiling point is used.

EXAMPLES

Typical examples and reference examples of the present invention are described below, but they should not be construed as limiting the scope of the invention.

Example 1

Production of N-Isopropyl-2-methylthioethylamine 1-1. Production of 2-Isopropylaminoethyl Hydrogensulfate In a 50-ml three-necked flask, 1.01 g (10 mmol) of sulfuric acid (97%) was diluted with 1 g of water, and the resulting dilution was ice-cooled. A mixture of 1.03 g (10 mmol) of 2-isopropylaminoethanol and 1 g of water was slowly dropped into the cooled dilution. After completion of the dropping, the resulting mixture was warmed to room temperature and 10 ml of toluene was added thereto. The mixture thus obtained was dehydrated by heating with vigorous stirring after attaching a Dean-Stark trap to the flask. The mixture was heated and stirred for 4 hours until a theoretical amount of water was removed. Then, the reaction was continued for another 1 hour. After a large portion of the toluene was removed by decantation, the residual toluene was distilled off under reduced pressure to obtain a crude product of 2-isopropylaminoethyl hydrogensulfate, the desired compound, quantitatively.

$^1$H-NMR ($\delta$ value, ppm/DMSO-$d_6$); 1.20 (d, 6H), 3.15 (br, 2H), 3.30 (br, 1H), 4.00 (br, 2H), 8.39 (br, 2H).

The following compounds were obtained in the same manner as above:

2-Phenylaminoethyl Hydrogensulfate $^1$H-NMR ($\delta$ value, ppm/DMSO-$d_6$); 3.50 (br, 2H), 3.97 (br, 2H), 7.20–7.55 (br, 7H).

2-Amino-2-methylpropyl Hydrogensulfate $^1$H-NMR ($\delta$ value, ppm/DMSO-$d_6$); 1.20 (s, 6H), 3.58 (br, 2H), 3.72 (s, 2H), 7.81 (br, 3H).

1-2. Production of N-Isopropyl-2-methylthioethylamine

In a mixed solvent of 5 ml of water and 5 ml of ethanol was suspended 0.69 g (5 mmol) of potassium carbonate, followed by adding thereto 0.92 g (5 mmol) of 2-isopropylaminoethyl hydrogensulfate and 2.8 g (6 mmol) of methylmercaptan sodium salt (15% aqueous solution), and the resulting mixture was gently refluxed for 8 hours. After completion of the reaction, the reaction mixture was cooled to room temperature and acidified with 6N hydrochloric acid. The aqueous layer was washed with ethyl acetate and made basic with an aqueous sodium hydroxide solution, and the desired compound was extracted three times with ethyl acetate. The combined organic layer was washed with saturated aqueous sodium chloride solution, dried over anhydrous sodium sulfate, and then distilled under reduced pressure to remove the solvent, whereby 0.47 g of N-isopropyl-2-methylthioethylamine was obtained (yield: 70%).

$^1$H-NMR ($\delta$ value, ppm/CDCl$_3$); 1.07 (d, 6H), 1.52 (br, 1H), 2.10 (s, 3H), 2.66 (t, 2H), 2.80 (t, 2H), 2.82 (m, 1H).

Example 2
Production of 2-Methyl-1-phenylthio-2-propylamine

In the same manner as in Example 1-1, 2-amino-2-methylpropyl hydrogensulfate was quantitatively obtained by using 2-amino-2-methyl-1-propanol as a starting material.

In 5 ml of water was dissolved 0.20 g (5 mmol) of sodium hydroxide, followed by adding thereto 0.85 g (5 mmol) of 2-amino-2-methylpropyl hydrogensulfate and 0.66 g (6 mmol) of thiophenol, and the resulting mixture was stirred at 80° C. for 8 hours. After completion of the reaction, the reaction mixture was cooled to room temperature and acidified with 6N hydrochloric acid. The aqueous layer was washed with ethyl acetate and made basic with an aqueous sodium hydroxide solution, and the desired compound was extracted three times with ethyl acetate. The combined organic layer was washed with saturated aqueous sodium chloride solution, dried over anhydrous sodium sulfate, and then distilled under reduced pressure to remove the solvent, whereby 0.52 g of 2-methyl-1-phenylthio-2-propylamine was obtained (yield: 57%).

$^1$H-NMR ($\delta$ value, ppm/CDCl$_3$); 1.20 (s, 6H), 1.42 (br, 2H), 3.03 (s, 2H), 7.16 (t, 1H), 7.28 (dd, 2H), 7.40 (dd, 2H).

Example 3
Production of 2-Methyl-1-methylthio-2-propylamine

In the same manner as in Example 1-1, 2-amino-2-methylpropyl hydrogensulfate was quantitatively obtained by using 2-amino-2-methyl-1-propanol as a starting material. This 2-amino-2-methylpropyl hydrogensulfate was used in the following reaction in the form of a toluene suspension without isolation.

The obtained suspension of 2-amino-2-methylpropyl hydrogensulfate (in an amount corresponding to 5 mmol) in toluene was ice-cooled, and a mixed solution of 0.24 g (6 mmol) of sodium hydroxide and 5 ml of water was added dropwise thereto. Then, 3.5 g (7.5 mmol) of methylmercaptan sodium salt (15% aqueous solution) was added thereto and stirred at 80° C. for 2 hours. After completion of the reaction, the reaction mixture was cooled to room temperature and acidified with 6N hydrochloric acid. The aqueous layer was washed with methyl t-butyl ether (MTBE) and made basic with an aqueous sodium hydroxide solution, and the desired compound was extracted three times with MTBE. The combined organic layer was washed with saturated aqueous sodium chloride solution, dried over anhydrous sodium sulfate, and then distilled under reduced pressure to remove the solvent, whereby 0.48 g of 2-methyl-1-methylthio-2-propylamine was obtained (yield: 81%).

$^1$H-NMR ($\delta$ value, ppm/CDCl$_3$); 1.17 (s, 6H), 1.43 (br, 2H), 2.17 (s, 3H), 2.56 (s, 2H).

Example 4
Production of 2-Methyl-1-n-octylthio-2-propylamine

In a mixed solvent of 10 ml of water and 10 ml of ethanol was suspended 1.38 g (10 mmol) of potassium carbonate. To the suspension were added 0.85 g (5 mmol) of 2-amino-2-methylpropyl hydrogensulfate and 0.73 g (5 mmol) of 1-octanethiol, and the resulting mixture was gently refluxed for 8 hours. After completion of the reaction, the reaction mixture was cooled to room temperature and the desired compound was extracted three times with ethyl acetate. The combined organic layer was washed with saturated aqueous sodium chloride solution, dried over anhydrous sodium sulfate, and then distilled under reduced pressure to remove the solvent, whereby 1.08 g of 2-methyl-1-n-octylthio-2-propylamine was obtained. The purity was measured in terms of area percentage by gas chromatography and found to be 91%.

Yield: 100%. $^1$H-NMR ($\delta$ value, ppm/CDCl$_3$); 0.87 (t, 3H), 1.16 (s, 1H), 1.20–1.60 (m, 14H), 2.54 (t, 2H), 2.57 (s, 2H).

Example 5
Production of 2-Methyl-1-n-octylthio-2-propylamine

2-Methyl-1-n-octylthio-2-propylamine was obtained (yield: 1.06 g) by carrying out the same reaction as in Example 4 except for changing the amount of potassium carbonate to 0.69 g (5 mmol). The purity was measured in terms of area percentage by gas chromatography and found to be 84%.

Example 6
Production of 2-Methyl-1-(2-pyridylthio)-2-propylamine

2-Methyl-1-(2-pyridylthio)-2-propylamine was obtained (yield: 83%) by carrying out the same reaction as in Example 4 except for using 2-pyridinethiol as a starting mercaptan.

$^1$H-NMR ($\delta$ value, ppm/CDCl$_3$); 1.20 (s, 6H), 1.52 (br, 2H), 3.35 (s, 2H), 6.96 (m, 1H), 7.21 (d, 1H), 7.44 (ddd, 1H), 8.38 (d, 1H).

The following compounds were produced in the same manner as in Example 4:

1-(4-t-Butylphenylthio)-2-methyl-2-propylamine (Yield: 69%)

$^1$H-NMR ($\delta$ value, ppm/CDCl$_3$); 1.21 (s, 6H), 1.29 (s, 9H), 1.86 (br, 2H), 3.03 (s, 2H), 7.30–7.35 (m, 4H).

1-(4-Chlorophenylthio)-2-methyl-2-propylamine (Yield: 57%)

$^1$H-NMR ($\delta$ value, ppm/CDCl$_3$); 1.21 (s, 6H), 1.84 (br, 2H), 3.02 (s, 2H), 7.20–7.28 (m, 2H), 7.29–7.35 (m, 2H).

2-Methyl-1-(2-naphthylthio)-2-propylamine (Yield: 45%)

$^1$H-NMR ($\delta$ value, ppm/CDCl$_3$); 1.24 (s, 6H), 1.55 (br, 2H), 3.14 (s, 2H), 7.38–7.50 (m, 3H), 7.70–7.82 (m, 4H).

1-(4-Chlorobenzylthio)-2-methyl-2-propylamine (Yield: 47%)

$^1$H-NMR ($\delta$ value, ppm/CDCl$_3$); 1.14 (s, 6H), 1.54 (br, 2H), 2.48 (s, 2H), 3.71 (s, 2H), 7.21–7.31 (m, 4H).

1-Ethylthio-2-methyl-2-propylamine (Yield: 72%)

$^1$H-NMR ($\delta$ value, ppm/CDCl$_3$); 1.17 (s, 6H), 1.25 (dt, 3H), 1.60–1.70 (br, 2H), 2.52–2.60 (m, 4H).

2-Methyl-1-n-propylthio-2-propylamine (Yield: 74%)

$^1$H-NMR ($\delta$ value, ppm/CDCl$_3$); 0.97 (t, 3H), 1.16 (s, 6H), 1.60 (m, 2H), 1.72 (br, 2H), 2.52 (t, 2H), 2.56 (s, 2H).

2-Methyl-1-i-propylthio-2-propylamine (Yield: 68%)

$^1$H-NMR ($\delta$ value, ppm/CDCl$_3$); 1.16 (s, 6H), 1.21–1.31 (m, 6H), 1.69 (br, 2H), 2.57 (s, 2H), 2.80–2.92 (m, 1H).

1-t-Butylthio-2-methyl-2-propylamine (Yield: 61%)

$^1$H-NMR ($\delta$ value, ppm/CDCl$_3$); 1.17 (s, 6H), 1.31 (s, 9H), 1.62 (br, 2H), 2.57 (s, 2H).

1-Methylthiomethyl-1-cyclopentylamine (Yield: 32%)
$^1$H-NMR (δ value, ppm/CDCl$_3$); 1.45–1.85 (m, 10H), 2.18 (s, 3H), 2.70 (s, 2H).
N,N-Dimethyl-2-methylthioethylamine (Yield: 83%)
$^1$H-NMR (δ value, ppm/CDCl$_3$); 2.13 (s, 3H), 2.26 (s, 6H), 2.48–2.65 (m, 4H).
1-Methylthio-2-propylamine (Yield: 68%)
$^1$H-NMR (δ value, ppm/CDCl$_3$); 1.15 (d, 3H), 1.49 (br, 2H), 2.10 (s, 3H), 2.36 (dd, 1H), 2.58 (dd, 1H), 3.00–3.12 (m, 1H).
2-Methylthio-N-phenylethylamine (Yield: 41%)
$^1$H-NMR (δ value, ppm/CDCl$_3$); 2.12 (s, 3H), 2.78 (t, 2H), 3.34 (t, 2H), 4.09 (br, 1H), 6.63 (dd, 2H), 6.73 (t, 1H), 7.19 (dd, 2H).
1-(2-Methylthioethyl)piperidine (Yield: 68%)
$^1$H-NMR (δ value, ppm/CDCl$_3$); 1.44 (br, 2H), 1.59 (br, 4H), 2.13 (s, 3H), 2.42 (br, 4H), 2.52–2.58 (m, 2H), 2.61–2.67 (m, 2H).
2-Methyl-1-(pyridine-N-oxide-2-ylthio)-2-propylamine (Yield: 60%)
$^1$H-NMR (δ value, ppm/CDCl$_3$); 1.28 (d, 3H), 1.8–2.0 (br, 2H), 2.83 (dd, 1H), 3.00 (dd, 1H), 3.28 (m, 1H), 7.05 (dt, 1H), 7.16–7.32 (m, 2H), 8.26 (d, 1H).
2-methyl-1-(3-pyridylthio)-2-propylamine (Yield: 67%)
H-NMR (δ value, ppm/CDCl$_3$); 1.14 (m, 3H), 1.7–1.9 (br, 2H), 2.85 (m, 1H), 2.94–3.10 (m, 2H), 7.19 (dd, 1H), 7.64 (d, 1H), 8.40 (d, 1H), 8.56 (s, 1H).
2-Methyl-1-(4-pyridylthio)-2-propylamine (Yield: 65%)
$^1$H-NMR (δ value, ppm/CDCl$_3$); 1.17 (d, 3H), 1.71 (bs, 2H), 3.03 (dd, 1H), 3.16 (m, 1H), 3.34 (dd, 1H), 6.95 (t, 1H), 7.16 (d, 1H), 7.41 (dt, 1H), 8.36 (d, 1H).
2-Methyl-1-(1H-1,2,4-triazol-3-ylthio)-2-propylamine (Yield: 40%)
$^1$H-NMR (δ value, ppm/CDCl$_3$); 1.24 (d, 3H), 2.96 (dd, 1H), 3.22 (dd, 1H), 3.36 (m, 1H), 7.99 (s, 1H).
3-Hydroxy-2-methyl-1-methylthio-2-propylamine (Yield: 54%)
$^1$H-NMR (δ value, ppm/CDCl$_3$); 1.12 (s, 3H), 2.16 (s, 3H), 2.28 (br, 2H), 2.61 (dd, 2H), 3.39 (dd, 2H).
1-Ethylthio-3-hydroxy-2-methyl-2-propylamine (Yield: 40%)
$^1$H-NMR (δ value, ppm/CDCl$_3$); 1.13 (s, 3H), 1.26 (t, 3H), 2.58 (dd, 2H), 2.64 (dd, 2H), 3.39 (dd, 2H).
1-(t-Butylphenylthio)-3-hydroxy-2-methyl-2-propylamine (Yield: 30%)
$^1$H-NMR (δ value, ppm/CDCl$_3$) 1.17 (s, 9H), 1.28 (s, 3H), 2.11 (br, 2H), 3.04 (dd, 2H), 3.39 (dd, 2H), 7.26–7.35 (m, 4H).
1-(2-Thienylthio)-2-propylamine (Yield: 78%)
$^1$H-NMR (δ value, ppm/CDCl$_3$); 1.14 (d, 3H), 2.61 (dd, 1H), 2.90 (dd, 1H), 3.05 (m, 1H), 6.97 (dd, 1H), 7.14 (dd, 1H), 7.34 (dd, 1H).
1-Ethylthio-2-propylamine (Yield: 72%)
$^1$H-NMR (δ value, ppm/CDCl$_3$); 1.14 (d, 3H), 1.25 (t, 3H), 1.51 (br, 2H), 2.36 (dd, 1H), 2.54 (q, 2H), 2.63 (dd, 1H), 3.03 (m, 1H).

Reference Example 1

Production of N$^1$-(4-Heptafluoroisopropyl-2-methylphenyl)-N$^2$-(1-methyl-2-methylthioethyl)-3-methylsulfonylphthalamide (Hereinafter Referred to as "Reference Compound 1") and N$^1$-(4-Heptafluoroisopropyl-2-methylphenyl)-N$^2$-(1-methyl-2-methylthioethyl)-6-methylsulfonylphthalamide (Hereinafter Referred to as "Reference Compound 2")

In 10 ml of dioxane was dissolved 0.63 g of N-(4-heptafluoroisopropyl-2-methylphenyl)-3-methylsulfonylphthalimide, followed by adding thereto 0.25 g of 1-methylthio-2-propylamine and 0.01 g of acetic acid, and the reaction was carried out with heating under reflux for 3 hours. After completion of the reaction, the solvent was distilled off under reduced pressure and the resulting residue was purified by silica gel column chromatography using a 1:1 mixed solvent of hexane and ethyl acetate as an eluent, to obtain 0.42 g of the desired compound (reference compound 1) having an Rf value of 0.5 to 0.7 and 0.18 g of the desired compound (reference compound 2) having an Rf value of 0.2 to 0.3.

Physical Property:

reference compound 1 m.p. 205–206° C. (Yield: 55%)

reference compound 2 m.p. 210–212° C. (Yield: 24%)

Reference Example 2

Insecticidal Effect on Diamondback Moth (*Plutella xylostella*)

Adult diamondback moths were released and allowed to oviposit on a Chinese cabbage seedling. Two days after the release, the seedling having eggs deposited thereon was immersed for about 30 seconds in a liquid chemical prepared by diluting a preparation containing each of the reference compounds as an active ingredient to adjust the concentration to 500 ppm. After air-drying, the seedling was allowed to stand in a room thermostated at 25° C. Six days after the immersion in the liquid chemical, the hatched insects were counted and the mortality was calculated according to the following equation. The test was carried out with three replications.

$$\text{Corrected mortality (\%)} = \frac{\begin{pmatrix}\text{Number of}\\\text{hatched insects}\\\text{in untreated}\\\text{group}\end{pmatrix} - \begin{pmatrix}\text{Number of}\\\text{hatched insects}\\\text{in treated}\\\text{group}\end{pmatrix}}{\begin{pmatrix}\text{Number of hatched insects}\\\text{in untreated group}\end{pmatrix}} \times 100$$

As a result, the reference compounds 1 and 2 were found to have a mortality of 100%.

Reference Example 3

Insecticidal Effect on Common Cutworm (*Spodoptera litura*)

A piece of cabbage leaf (cultivar: Shikidori) was immersed for about 30 seconds in a liquid chemical prepared by diluting a preparation containing each of the reference compounds as an active ingredient to adjust the concentration to 500 ppm. After air-drying, the piece was placed in a plastic Petri dish with a diameter of 9 cm whose bottom had been covered with a wetted filter paper. The piece was inoculated with third-instar larvae of common cutworm and the Petri dish was allowed to stand in a room thermostated at 25° C. and having a relative humidity of 70%. Eight days after the inoculation, the dead and alive were counted and the mortality was calculated according to the following equation. The test was carried out with three replications of 10 insects.

As a result, the reference compound 1 was found to have a mortality of 100%.

What is claimed is:

1. A process for producing a thioalkylamine represented by formula (I):

(wherein $R_1$, $R_2$, $R_3$, $R_4$, $R_5$, $R_6$ and R are as defined below), characterized by reacting sulfuric acid with an amino alcohol represented by formula (II):

(wherein each of $R_1$ and $R_2$, which may be the same or different, is a hydrogen atom; a $(C_1-C_4)$alkyl group; a $(C_3-C_8)$cycloalkyl group; a $(C_3-C_8)$cycloalkyl$(C_1-C_4)$alkyl group; a hydroxy$(C_1-C_4)$alkyl group; a phenyl group; a substituted phenyl group having 1 to 5 substituents which may be the same or different and each of the substituents is selected from a halogen atom, a cyano group, a nitro group, a $(C_1-C_4)$alkyl group, a halo$(C_1-C_4)$alkyl group, a $(C_3-C_8)$cycloalkyl group, a $(C_1-C_4)$alkoxy group, a halo$(C_1-C_4)$alkoxy group, a $(C_1-C_4)$alkylthio group, a halo$(C_1-C_4)$alkylthio group, a $(C_1-C_4)$alkylsulfinyl group, a halo$(C_1-C_4)$alkylsulfinyl group, a $(C_1-C_4)$alkylsulfonyl group, a halo$(C_1-C_4)$alkylsulfonyl group, a carboxyl group, a $(C_1-C_4)$alkoxycarbonyl group, a $(C_1-C_4)$alkoxy$(C_1-C_4)$alkyl group, $R_7$—C(=O)— (wherein $R_7$ is a $(C_1-C_4)$alkyl group, a halo$(C_1-C_4)$alkyl group, a phenyl group or a phenoxy group), an amino group, and a substituted amino group having one or two substituents which may be the same or different and are selected from $(C_1-C_4)$alkyl groups; a substituted phenyl group having as the substituent a $(C_3-C_4)$alkylene group or a $(C_1-C_2)$alkylenedioxy group, which forms a ring together with a pair of adjacent carbon atoms in the benzene ring; a phenyl$(C_1-C_4)$alkyl group; or a substituted phenyl$(C_1-C_4)$alkyl group having on the ring 1 to 5 substituents which may be the same or different and each of the substituents is selected from a halogen atom, a cyano group, a nitro group, a $(C_1-C_4)$alkyl group, a halo$(C_1-C_4)$alkyl group, a $(C_3-C_8)$cycloalkyl group, a $(C_1-C_4)$alkoxy group, a halo$(C_1-C_4)$alkoxy group, a $(C_1-C_4)$alkylthio group, a halo$(C_1-C_4)$alkylthio group, a $(C_1-C_4)$alkylsulfinyl group, a halo$(C_1-C_4)$alkylsulfinyl group, a $(C_1-C_4)$alkylsulfonyl group and a halo$(C_1-C_4)$alkylsulfonyl group; $R_1$ and $R_2$ may form a $(C_2-C_5)$alkylene group by binding to each other; $R_1$ and $R_3$ or $R_5$ may form a $(C_3-C_5)$alkylene group by binding to each other, each of $R_3$ and $R_4$, which may be the same or different, is a hydrogen atom or a $(C_1-C_4)$alkyl group; $R_3$ and $R_4$ may form a $(C_4-C_6)$alkylene group by binding to each other; $R_3$ and $R_5$ may form a $(C_2-C_4)$alkylene group by binding to each other, each of $R_5$ and $R_6$, which may be the same or different, is a hydrogen atom; a $(C_1-C_4)$alkyl group; a phenyl group; a substituted phenyl group having 1 to 5 substituents which may be the same or different and each of the substituents is selected from a halogen atom, a cyano group, a nitro group, a $(C_1-C_4)$alkyl group, a halo$(C_1-C_4)$alkyl group, a $(C_3-C_8)$cycloalkyl group, a $(C_1-C_4)$alkoxy group, a halo$(C_1-C_4)$alkoxy group, a $(C_1-C_4)$alkylthio group, a halo$(C_1-C_4)$alkylthio group, a $(C_1-C_4)$alkylsulfinyl group, a halo$(C_1-C_4)$alkylsulfinyl group, a $(C_1-C_4)$alkylsulfonyl group and a halo$(C_1-C_4)$alkylsulfonyl group; a phenyl$(C_1-C_4)$alkyl group; or a substituted phenyl$(C_1-C_4)$alkyl group having on the ring 1 to 5 substituents which may be the same or different and each of the substituents is selected from a halogen atom, a cyano group, a nitro group, a $(C_1-C_4)$alkyl group, a halo$(C_1-C_4)$alkyl group, a $(C_3-C_8)$cycloalkyl group, a $(C_1-C_4)$alkoxy group, a halo$(C_1-C_4)$alkoxy group, a $(C_1-C_4)$alkylthio group, a halo$(C_1-C_4)$alkylthio group, a $(C_1-C_4)$alkylsulfinyl group, a halo$(C_1-C_4)$alkylsulfinyl group, a $(C_1-C_4)$alkylsulfonyl group and a halo$(C_1-C_4)$alkylsulfonyl group; and $R_5$ and $R_6$ may form a $(C_4-C_6)$alkylene group by binding to each other) to obtain a sulfate ester represented by formula (III):

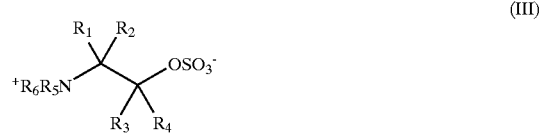

(wherein $R^1$, $R_2$, $R_3$, $R_4$, $R_5$ and $R_6$ are as defined above), and reacting the sulfate ester, after or without isolation, with a mercaptan represented by formula (IV):

RSM          (IV)

(wherein R is a $(C_1-C_{12})$alkyl group; a $(C_3-C_8)$cycloalkyl group; a $(C_3-C_8)$cycloalkyl$(C_1-C_4)$alkyl group; a phenyl group; a substituted phenyl group having 1 to 5 substituents which may be the same or different and each of the substituents is selected from a halogen atom, a $(C_1-C_6)$alkyl group, a halo$(C_1-C_3)$alkyl group, a $(C_3-C_8)$cycloalkyl group, a $(C_1-C_4)$alkoxy group and a halo$(C_1-C_4)$alkoxy group; a phenyl$(C_1-C_4)$alkyl group; a substituted phenyl $(C_1-C_4)$alkyl group having on the ring 1 to 5 substituents which may be the same or different and each of the substituents is selected from a halogen atom and a $(C_1-C_4)$alkyl group; a naphthyl group; an aromatic heterocyclic group; or a substituted aromatic heterocyclic group having one or more substituents which may be the same or different and each of the substituents is selected from a halogen atom, a $(C_1-C_4)$alkyl group, a $(C_1-C_4)$alkoxy group, a phenyl group and a substituted phenyl group having 1 to 5 substituents which may be the same or different and each of the substituents is selected from a halogen atom and a $(C_1-C_4)$alkyl group, and M is a hydrogen atom, an ammonium group or an alkali metal atom).

2. A process for producing a thioalkylamine represented by formula (I):

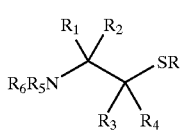
(I)

(wherein $R_1$, $R_2$, $R_3$, $R_4$, $R_5$, $R_6$ and R are as defined below), characterized by reacting a sulfate ester represented by formula (III):

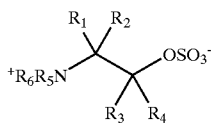
(III)

(wherein each of $R_1$ and $R_2$, which may be the same or different, is a hydrogen atom; a ($C_1$–$C_4$)alkyl group; a ($C_3$–$C_8$)cycloalkyl group; a ($C_3$–$C_8$)cycloalkyl($C_1$–$C_4$)alkyl group; a hydroxy($C_1$–$C_4$)alkyl group; a phenyl group; a substituted phenyl group having 1 to 5 substituents which may be the same or different and each of the substituents is selected from a halogen atom, a cyano group, a nitro group, a ($C_1$–$C_4$)alkyl group, a halo($C_1$–$C_4$)alkyl group, a ($C_3$–$C_8$)cycloalkyl group, a ($C_1$–$C_4$)alkoxy group, a halo($C_1$–$C_4$)alkoxy group, a ($C_1$–$C_4$)alkylthio group, a halo($C_1$–$C_4$)alkylthio group, a ($C_1$–$C_4$)alkylsulfinyl group, a halo($C_1$–$C_4$)alkylsulfinyl group, ($C_1$–$C_4$)alkylsulfonyl group, a halo($C_1$–$C_4$)alkylsulfonyl group, a carboxyl group, a ($C_1$–$C_4$)alkoxycarbonyl group, a ($C_1$–$C_4$)alkoxy($C_1$–$C_4$) alkyl group, $R_7$—C(=O)— (wherein $R_7$ is a ($C_1$–$C_4$)alkyl group, a halo($C_1$–$C_4$)alkyl group, a phenyl group or a phenoxy group), an amino group, and a substituted amino group having one or two substituents which may be the same or different and are selected from ($C_1$–$C_4$)alkyl groups; a substituted phenyl group having as the substituent a ($C_3$–$C_4$) alkylene group or a ($C_1$–$C_2$)alkylenedioxy group, which forms a ring together with a pair of adjacent carbon atoms in the benzene ring; a phenyl($C_1$–$C_4$)alkyl group; or a substituted phenyl($C_1$–$C_4$)alkyl group having on the ring 1 to 5 substituents which may be the same or different and each of the substituents is selected from a halogen atom, a cyano group, a nitro group, a ($C_1$–$C_4$)alkyl group, a halo ($C_1$–$C_4$)alkyl group, a ($C_3$–$C_8$)cycloalkyl group, a ($C_1$–$C_4$) alkoxy group, a halo($C_1$–$C_4$)alkoxy group, a ($C_1$–$C_4$) alkylthio group, a halo($C_1$–$C_4$)alkylthio group, a ($C_1$–$C_4$) alkylsulfinyl group, a halo($C_1$–$C_4$)alkylsulfinyl group, a ($C_1$–$C_4$)alkylsulfonyl group and a halo($C_1$–$C_4$)alkylsulfonyl group; $R_1$ and $R_2$ may form a ($C_2$–$C_5$)alkylene group by binding to each other; $R_1$ and $R_3$ or $R_5$ may form a ($C_3$–$C_5$)alkylene group by binding to each other, each of $R_3$ and $R_4$, which may be the same or different, is a hydrogen atom or a ($C_1$–$C_4$)alkyl group; $R_3$ and $R_4$ may form a ($C_4$–$C_6$)alkylene group by binding to each other; $R_3$ and $R_5$ may form a ($C_2$–$C_4$)alkylene group by binding to each other, each of $R_5$ and $R_6$, which may be the same or different, is a hydrogen atom; a ($C_1$–$C_4$)alkyl group; a phenyl group; a substituted phenyl group having 1 to 5 substituents which may be the same or different and each of the substituents is selected from a halogen atom, a cyano group, a nitro group, a ($C_1$–$C_4$)alkyl group, a halo($C_1$–$C_4$)alkyl group, a ($C_3$–$C_8$)cycloalkyl group, a ($C_1$–$C_4$)alkoxy group, a halo($C_1$–$C_4$)alkoxy group, a ($C_1$–$C_4$)alkylthio group, a halo($C_1$–$C_4$)alkylthio group, a ($C_1$–$C_4$)alkylsulfinyl group, a halo($C_1$–$C_4$) alkylsulfinyl group, a ($C_1$–$C_4$)alkylsulfonyl group and a halo($C_1$–$C_4$)alkylsulfonyl group; a phenyl($C_1$–$C_4$) alkyl group; or a substituted phenyl($C_1$–$C_4$)alkyl group having on the ring 1 to 5 substituents which may be the same or different and each of the substituents is selected from a halogen atom, a cyano group, a nitro group, a ($C_1$–$C_4$)alkyl group, a halo($C_1$–$C_4$)alkyl group, a ($C_3$–$C_8$)cycloalkyl group, a ($C_1$–$C_4$)alkoxy group, a halo($C_1$–$C_4$)alkoxy group, a ($C_1$–$C_4$)alkylthio group, a halo($C_1$–$C_4$)alkylthio group, a ($C_1$–$C_4$)alkylsulfinyl group, a halo($C_1$–$C_4$)alkylsulfinyl group, a ($C_1$–$C_4$) alkylsulfonyl group and a halo($C_1$–$C_4$)alkylsulfonyl group; and $R_5$ and $R_6$ may form a ($C_4$–$C_6$)alkylene group by binding to each other) with a mercaptan represented by formula (IV):

$$RSM \qquad (IV)$$

(wherein R is a ($C_1$–$C_{12}$)alkyl group; a ($C_3$–$C_8$)cycloalkyl group; a ($C_3$–$C_8$)cycloalkyl($C_1$–$C_4$)alkyl group; a phenyl group; a substituted phenyl group having 1 to 5 substituents which may be the same or different and each of the substituents is selected from a halogen atom, a ($C_1$–$C_6$)alkyl group, a halo($C_1$–$C_3$)alkyl group, a ($C_3$–$C_8$)cycloalkyl group, a ($C_1$–$C_4$)alkoxy group and a halo($C_1$–$C_4$)alkoxy group; a phenyl($C_1$–$C_4$)alkyl group; a substituted phenyl ($C_1$–$C_4$)alkyl group having on the ring 1 to 5 substituents which may be the same or different and each of the substituents is selected from a halogen atom and a ($C_1$–$C_4$)alkyl group; a naphthyl group; an aromatic heterocyclic group; or a substituted aromatic heterocyclic group having one or more substituents which may be the same or different and each of the substituents is selected from a halogen atom, a ($C_1$–$C_4$)alkyl group, a ($C_1$–$C_4$)alkoxy group, a phenyl group and a substituted phenyl group having 1 to 5 substituents which may be the same or different and each of the substituents is selected from a halogen atoms and a ($C_1$–$C_4$) alkyl group, and M is a hydrogen atom, an ammonium group or an alkali metal atom) in the presence of a base.

* * * * *